United States Patent [19]

Ho et al.

[11] 4,042,879

[45] Aug. 16, 1977

[54] MICROWAVE AEROSOL WATEROMETER

[75] Inventors: William W. Ho, Thousand Oaks; Ronald M. Govan, Camarillo, both of Calif.

[73] Assignee: Rockwell International Corporation, El Segundo, Calif.

[21] Appl. No.: 628,694

[22] Filed: Nov. 3, 1975

[51] Int. Cl.² .......................................... G01R 27/04
[52] U.S. Cl. .............................................. 324/58.5 C
[58] Field of Search .............. 324/58.5 C, 58 C, 61 R; 73/29, 23

[56] References Cited

U.S. PATENT DOCUMENTS

| | | | |
|---|---|---|---|
| 2,423,383 | 7/1947 | Hershberger | 324/58.5 C X |
| 2,457,673 | 12/1948 | Hershberger | 324/58.5 C |
| 2,580,968 | 1/1952 | Sproull | 324/58 C |
| 2,792,548 | 5/1947 | Hershberger | 324/58.5 C |
| 2,882,493 | 4/1959 | Dicke | 324/58.5 C |
| 2,964,703 | 12/1960 | Sargent et al. | 324/58.5 C |
| 3,238,452 | 3/1966 | Schmitt et al. | 324/61 R |

FOREIGN PATENT DOCUMENTS 1,302,380  1/1973  United Kingdom ..................... 73/29

Primary Examiner—Stanley T. Krawczewicz
Attorney, Agent, or Firm—L. Lee Humphries; Henry Kolin; Clark E. DeLarvin

[57] ABSTRACT

A gaseous medium containing aerosols is drawn through a quartz sampling tube and a filter located therein, with the aerosols becoming entrapped on the filter. The filter is located at the geometric center of a microwave cavity, and the principal resonance of the latter is tracked with the aid of an adaptive electronic circuit. The time rate of change of the resonant frequency is a function of the rate of deposition of particulate matter on the filter, and principally of the liquid water content of those aerosols. Water in the vapor phase passes through the filter and does not affect the measurement; solid particulate does affect the frequency shift but in a second order manner and is readily compensated for after measurement of total aerosol mass deposited and the determination of the dielectric constant of the solid species therein. In a preferred embodiment a pair of microwave cavities is utilized to compare the resonant shift with the resonant frequency indicated for the same air sample after removal of the aerosol.

11 Claims, 4 Drawing Figures

MICROWAVE AEROSOL WATEROMETER

BACKGROUND OF THE INVENTION

This invention relates to the detection and quantitative measurement of liquid water droplets entrained in atmospheric air and other gaseous media. It relates, more particularly, to such detection and measurement utilizing a resonant microwave cavity.

Water is present in the atmosphere in three forms: as vapor; chemically bound in solid dust particles many of whose constituents are hydrates; and in the form of condensed droplets. This latter form has been, traditionally, felt to exist only in fogs and clouds when the local humidity approached 100%. Recent research, arising from the intense concern with the properties and activity of contaminants in urban air spaces, has indicated that liquid water is present in substantial quantities even at relatively low water vapor pressures. Such water droplets are generally condensates forming on hygroscopic solid dust particles, and may be present at relative humidities as low as 50%.

These water particles have considerable influence on the physical and chemical acitivty of the atmosphere, and the detection of their presence and the measurement of their mass density in the air are of substantial importance. For example, the small droplets of water refract sunlight and materially contribute to conditions of haze, while their ability to dissolve gaseous chemical species present in the air greatly enhances the chemical activity of the latter.

Methods of the prior art are not readily adapted to the measurement of such particulate liquid water. Measurements made by such methods either lump all water species present — chemically bound or free, liquid or vapor — into a single measure of water concentration, or they are sensitive only to the vapor phase, resulting in conventional measurements of relative humidity.

It is, therefore, the primary object of the invention to provide method and means for the detection and measurement of liquid water particles in atmospheric air which is essentially insensitive to the presence of unbound water vapor and to the presence of chemically bound water in solid hydrates.

It is a further object of the invention to provide a detector for liquid water particles in air and other gases which is based on readily reproducible physical phenomena and which relies on the dielectric properties of such water.

It is another object of the invention to provide such a detector wherein the quantitative measurements are based on the changes in the resonant frequency of a microwave cavity.

SUMMARY OF THE INVENTION

In one aspect, the present invention is a method for the determination of the liquid water content of aerosols dispersed in a gaseous medium, comprising the steps of: trapping the particulate content of a known quantity of such a medium inside a microwave cavity of known resonant frequency; determining the resonant frequency with the particulate trapped therein; and relating the change in that resonant frequency, through known physical constants defining the properties of the entrapped particulate fraction, to the quantity of liquid water present in the original sample.

In another aspect, the present invention encompasses apparatus wherein the aforementioned method may be performed and the liquid water component of an aerosol borne in a gaseous medium determined.

Such apparatus comprise:

a. A microwave cavity of known resonant frequency;

b. Means for passing a predetermined quantity of aerosol-bearing gaseous medium through said cavity;

c. Filter means within said cavity, for capturing the aerosol particles from the gaseous medium; and d. Means for determining the change in the resonant frequency of said cavity, due to the captured particulate entrained in the filter means.

The aerosols trapped in such filtering devices within the resonant cavity will include solid dust particles, liquid water condensed around such dust particles, as well as aqueous solutions so condensed. Because of the substantially higher dielectric constant of the liquid water, as compared to the other species, present, the contribution of the liquid water droplets to the frequency shift of the cavity will be very large. Fairly crude estimates of the density and dielectric constant of the other species will permit the determination of the fraction of captured particulate which is liquid water.

In one embodiment of the invention the gaseous medium is drawn continuously through the resonant cavity and the time rate of the frequency shift in the resonance of the cavity related to the flow rate of the medium to yield a measure of the quantity of water in liquid form in a typical volume of the medium.

In another embodiment of the invention a pair of resonant cavities are employed, one of them serving as a frequency reference, and the gaseous medium drawn through them in tandem. The particulate matter is captured in the first cavity, but any changes in the temperature, density or humidity of the gas itself which would result in second order changes in the reference frequency will be automatically compensated for by comparing the outputs of the tandem detectors.

BRIEF DESCRIPTION OF THE ACCOMPANYING DRAWINGS

The invention will be described in detail with reference to the drawings, wherein.

DESCRIPTION OF THE PREFERRED EMBODIMENT

Figure 1:
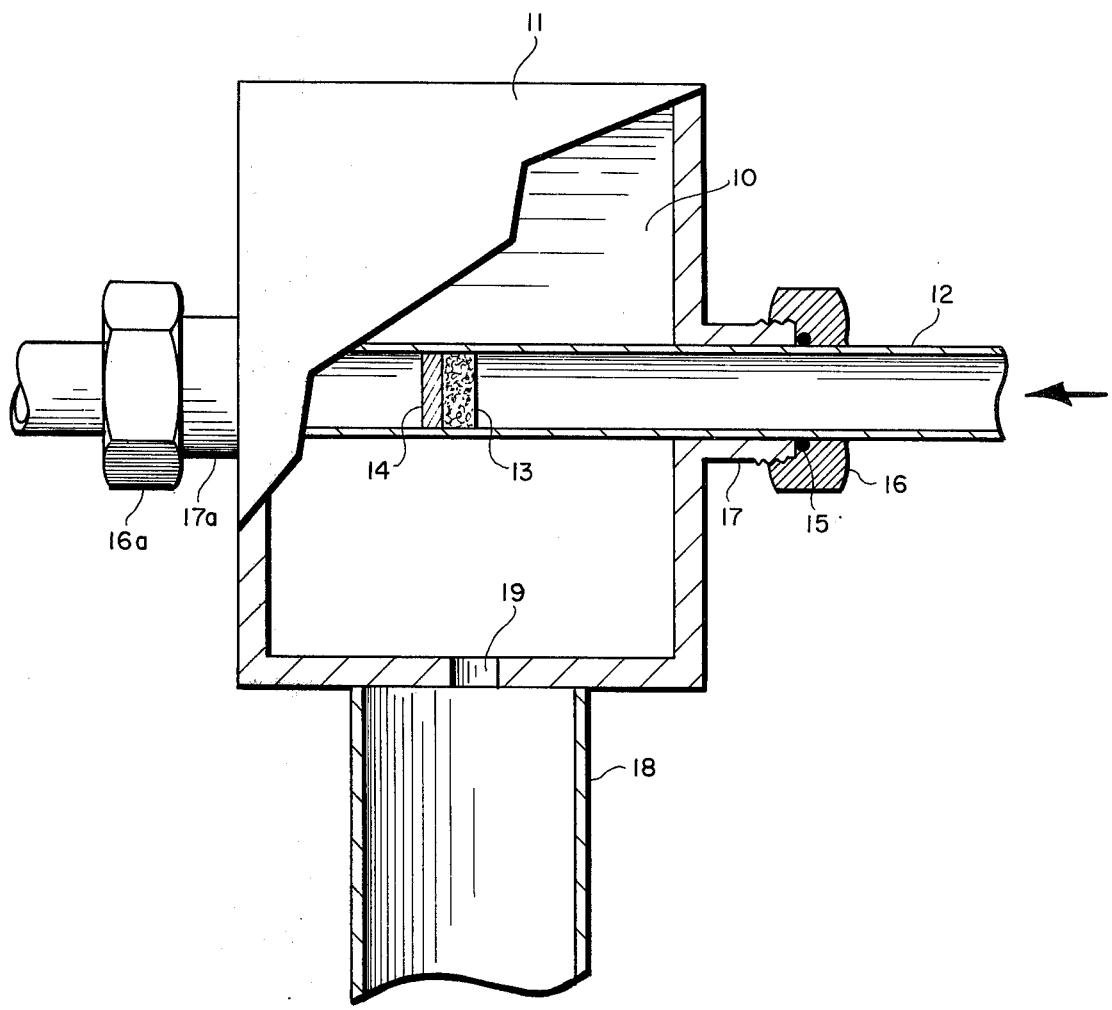
FIG. 1 is a transverse view, in partial section, through a detector as employed in the invention, incorporating a filter centrally located in a microwave cavity of known resonant frequency.

The transverse, partially sectioned, view of FIG. 1 shows a cylindrical microwave cavity 10 enclosed by a housing 11. The form and resonant mode of the cavity 10 is generally known in the art as $TM_{010}$ and for purposes of liquid water detection according to the instant invention the dimensions thereof may be chosen so that the resonant frequency of the cavity lies in the region between 2 and 4 Gigaherz.

The housing 11 is advantageously formed of Invar or some other material with small temperature coefficient of expansion in the operating range, so that the resonant characteristic of the cavity 10 shall not be materially affected by variations in atmospheric temperature. The same purpose may be served by the provision of heating and/or cooling devices to maintain the housing 11 at a constant temperature; or the provision of such controls may be combined with construction from a temperature-insensitive alloy.

A tube 12, transparent to microwave radiation in the chosen frequency band, constructed of quartz for example, passes through the axis of the cavity 10 and is sealed by means of a seal ring 15 entrapped between a boss 17 and a nut 16 at the input end of the housing 11. Similarly, at the distal end of the housing 11 there is a seal ring (not shown) entrapped between nut 16a and boss 17a.

A gaseous medium bearing finely divided solid and liquid matter is drawn through the tube 12 by means of a vacuum pump. In passing through the cavity 10, inside the tube 12, the particles suspended in the gas encounter a filter disk 13 supported on a plate 14. The plate 14 is an assembly of fused segments of quartz hypodermic tubing; it has substantial porosity to the passage of gas, yet provides a substantially solid backing to the fragile filter 13.

The filter 13 is advantageously constructed from glass or quartz fiber, providing both good entrapment qualities for particulates, including the submicroscopic spherules of liquid water which are the target of the detection and measurement apparatus of the invention.

A waveguide 18 is also provided, attached to the periphery of the housing 11 and communicating with the cavity 10 therein through an orifice 19. The waveguide couples the cavity 10 to the overall microwave circuitry wherein the radiation resonating inside the cavity is generated and the properties of the cavity monitored.

Figure 2:
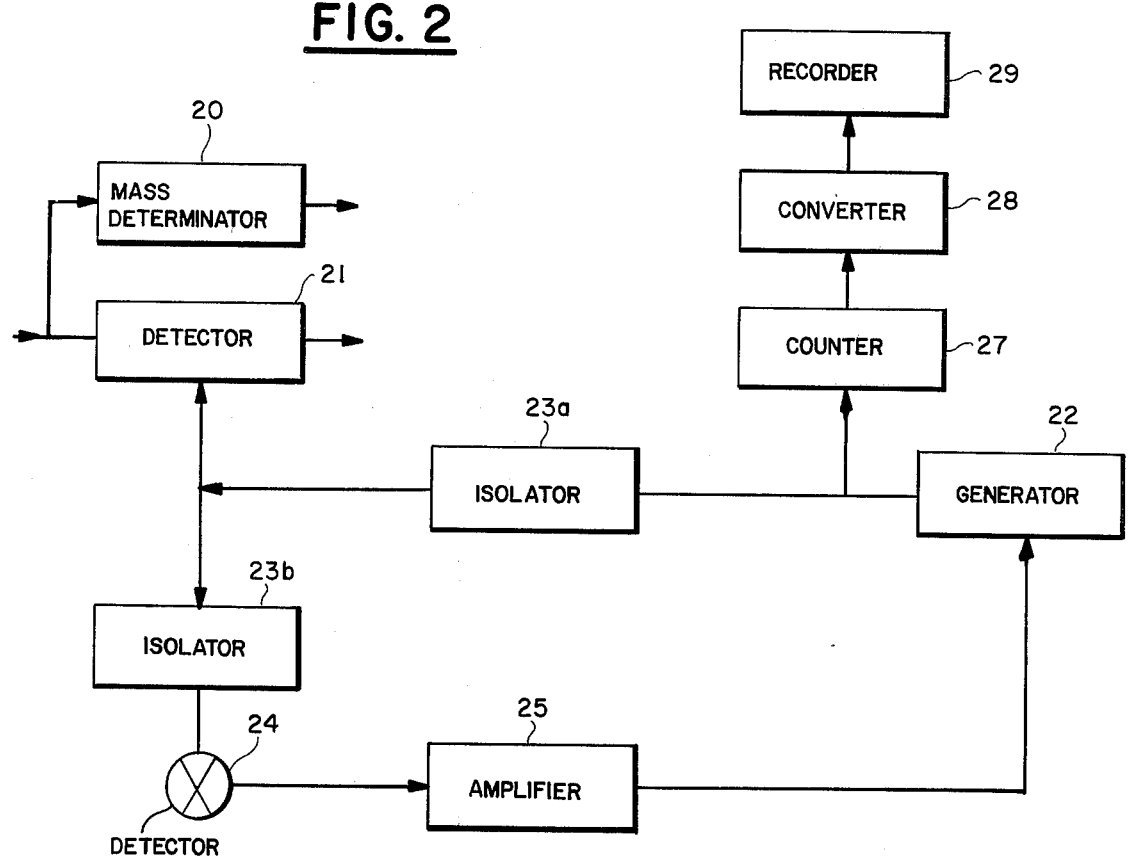
FIG. 2 is a schematic circuit diagram of the microwave network of the invention, employing a detector similar to that shown in FIG. 1.

Turning to the schematic diagram of FIG. 2, a detector 21 is seen, constructed in the same manner as the detector of FIG. 1 with an enclosed cavity of known resonant frequency, and a sample tube for ingesting a pre-determined volume of gas and a filter for retaining within the cavity the particulate aerosol borne by that gas.

Input to the detector originates in the microwave signal generator 22, suitably a stable FM source whose output frequency may be altered in response to a voltage signal. The output wave of the signal generator 22 is fed into the detector 21 via an isolator 23a. The resonant mode output of the detector 21 is sensed by a crystal detector 24, also isolated from the detector by an isolator 23b. The output of the crystal detector is fed into a lock-in amplifier 25, the output of which is used to adjust the output frequency of the signal generator 22 to the instantaneous resonant frequency of the water detector 21.

In this manner the output signal of the signal generator always tracks the resonant frequency of the cavity 10 incorporated in the detector 21. The output frequency is sensed by a pulse counter 27 — providing an instantaneous readout of the resonant frequency — and is also recorded by an analog device 29, after processing the counter output signal through a digital-to-analog converter 28. The interconnection between the several components of the circuit of FIG. 2 is by means of cables and waveguides as suited to the particular signal being transmitted.

In using the apparatus schematically depicted in FIG. 2, a vacuum pump is first turned on and the inlet of the sampling tube 12 — or its functional equivalent — exposed to the gaseous medium to be tested for the presence of liquid water entrained therein as an aerosol. To permit calbration, the stream is initially passed through an external filter to ensure the retention of all solid and liquid particulate outside of the detector 21. In this manner the electronic circuit can be tuned to the resonant frequency of the empty cavity 10, as modified by the presence of a volume of the gaseous medium inside the tube 12.

The external filter is then removed and the gas — for example atmospheric air — with its full aerosol content permitted to enter the cavity, with the particulate species depositing on the filter 13. As the amount of such particulate increases, the natural frequency of the system drifts away from the value recorded empty, and the change is observed at the frequency meter 28 and recorded on the chart of recorder 29.

The arrangement of FIG. 2 is capable of tracking the resonance to within one part in $10^7$, in the frequency range of 3 Gigaherz.

The frequency shift can be related to the total amount of liquid water on the filter 13 by means of simple equations incorporating the total retained means on the filter and the mean dielectric constant of the solid species therein. Therefore, the total mass of the retained particulate must be determined.

In a preferred embodiment of the invention, the total mass is determined by a device, such as a beta gauge for collecting and determining the total suspended mass of particulate matter in a comparable sample of air.

Figure 4:
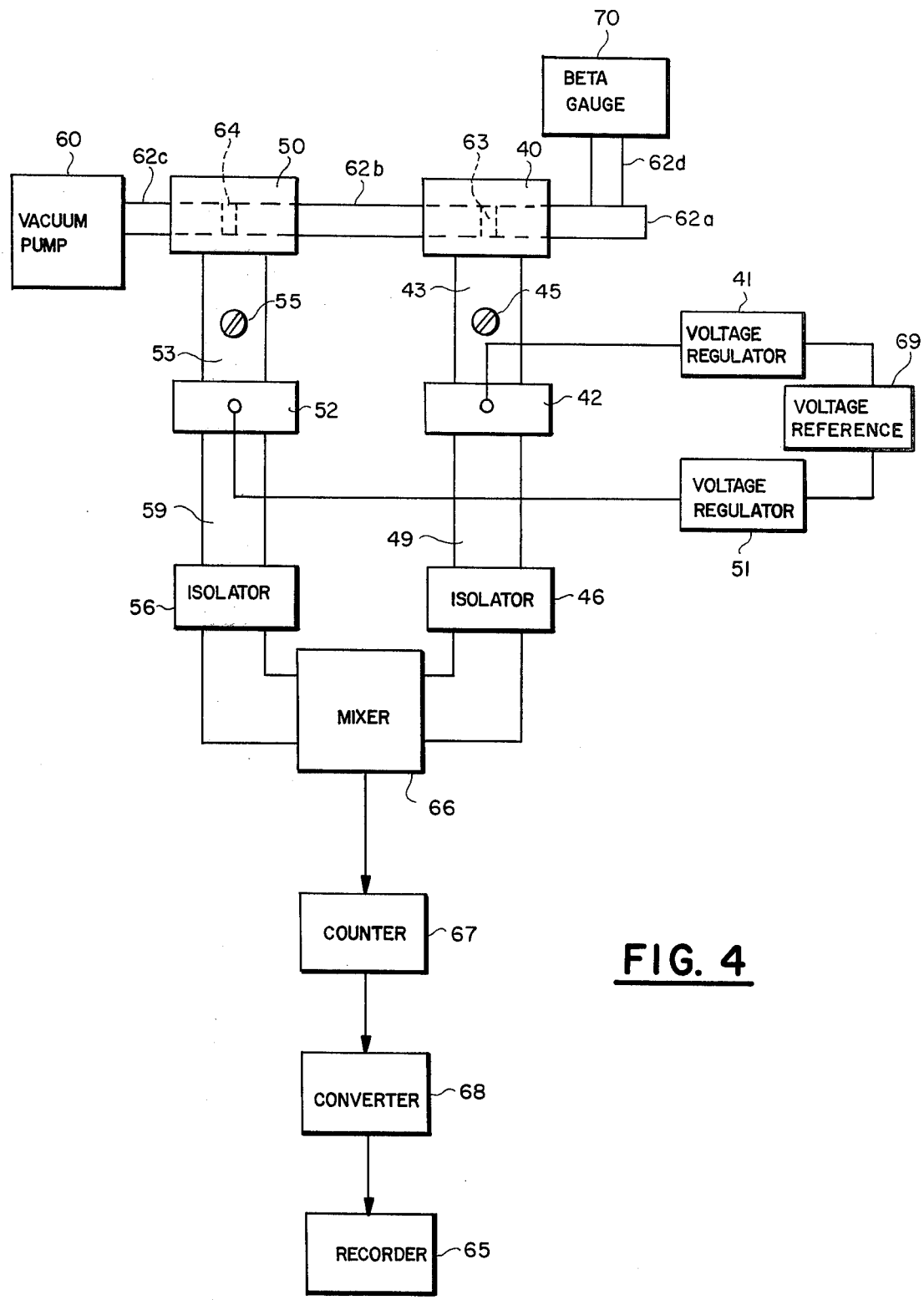
FIG. 4 is a schematic circuit diagram of an embodiment of the invention employing measuring and reference detectors similar to that shown in FIG. 1 in tandem.

This is illustrated, for example by the arrangements shown in FIGS. 2 and 4. In FIG. 2 air to be sampled passes into the detector 21 through the indicated air inlet lines, so arranged that an air sample passes through mass determinator 20. This may be accomplished by dividing the incoming air stream, or, in the alternative, providing separate inlets for the detector 21 and mass determinator 20. The "beta gauge" referred to above is a commercially available device which utilizes a filter to collect particulate matter in the air sample and which has a source of beta radiation impinging on the filter, as well as means for detecting the amount of beta radiation passing through the filter. The attenuation of the radiation passing the filter is a function of the total mass collected on the filter.

It has been experimentally determined that the mass of liquid-aerosol water can be calculated from the frequency shift, after determining the total mass of material collected on the filter, by the following equation: $M_2 = AF - BM_t$ where $M_2$ = the mass of water in micrograms; $M_t$ = the total mass collected on the filter in micrograms, $F$ = the shift in resonant frequency in KHZ, and A and B are specific constants dependent on the parameters of the system, including the volume of the detector cavity, the frequency, and the dielectric constants of water and the solid material collected on the filter.

It is to be noted that the measurement is sensitive only to free or chemically unbound water because hydrates have much lower dielectric constants than non-associated water.

The ultimate reduction to liquid water content, expressed in micrograms per cubic meter or analogous quantities, relies on the relationship between the time rate of change of the frequency shift and the pumping rate of the vacuum pump, in addition to the previously mentioned mass determination.

Gunn effect devices, with their ability to track the resonant characteristic of a microwave cavity, have been found particularly suitable for use in the instrument of the invention.

Figure 3:
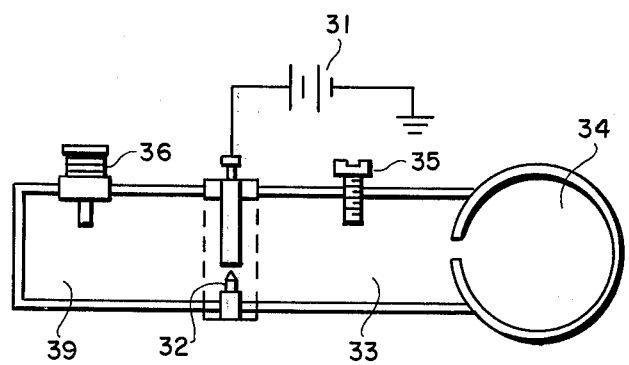
FIG. 3 is a section through a Gunn oscillator as employed in an alternate embodiment of the invention.

A typical Gunn resonator is shown in the sectioned view of FIG. 3, wherein 32 identifies a Gunn Diode Oscillator operated in the 'dual-beam' mode between a half-wave transmission cavity 33 provided with a tuning screw 35 and a reflector cavity 39. The transmission cavity 33 is coupled to a resonant cavity 34, analogous to the cavity 10 of FIG. 1, adapted to use as the measurement station of a liquid water detector. A stable voltage source 31 powers the Gunn Diode, and a coaxial fitting 36 is used to pick up the resulting signal, which is locked in frequency to the instantaneous resonance of the cavity 34.

In tests, the circuit of FIG. 3, using a $TM_{010}$ mode resonant cavity 34, was found to be able to be stably tracking the resonance of the cavity to within 1 part in $10^7$, in the frequency band around 9 Gigaherz. $TM_{010}$ refers to a transverse magnetic wave in the 010 direction.

An embodiment of the instrument of the invention, employing two Gunn Diode circuits is illustrated in the partially schematic diagram of FIG. 4.

A common voltage reference 69 is employed to control paired voltage regulators 41 and 51 which power Gunn Diode Oscillators 42 and 52, respectively. Transmission cavities 43 and 49 flank the oscillator 42, with feeds into a measurement cavity 40 and an isolator 46, respectively. Similar transmission cavities 53 and 59 feed a reference cavity 50 and an isolator 56 from the oscillator 52. Tuning screws 45 and 55 are used to fine-tune the parallel resonant circuits.

A gaseous medium is drawn through a continuous channel, formed of segments 62a, 62b and 62c, into a vacuum pump 60. Particulate matter borne in the gaseous medium is trapped in a filter 63 centrally located inside the measurement cavity 40. A similar filter structure 64 is located centrally in the reference cavity 50, to provide the same geometric and dielectric constants for the operation of the latter. The gaseous medium cleansed of its particulate components is discharged from the pump 60.

In the operation of the device, the filter 63 is first renewed, and a particulate free gas passed through the channel 62. The resonant microwave system is then tuned, by use of the tuning screws 45 and 55, to a common base frequency. The congruence of the two frequencies is detected by the summing circuit of the instrument, including a mixer 66 and a frequency counter 67. With both sides of the unit at the same base frequency the output of the counter 67 is zero.

When the unit is properly calibrated, the gaseous medium to be analyzed for its content of liquid water in suspension is passed through the channel 62 and the particulates thereof trapped on the filter 63. As aerosol particles accumulate on the filter, the resonant frequency of the cavity 40 will change with respect to the resonant frequency of the reference cavity 50, and the mixer output, as signaled by the frequency counter, will change from the zero beat frequency to reflect the change in properties of the cavity 40.

Since both cavities are essentially identical in size, shape and construction, minor changes in their resonances due to changes in temperature, transient changes in the composition of the gas flowing through them, or other environmental factors, are automatically compensated for and are not reflected in the instrument output.

Since the accumulation of particulate matter on the filter 63 is a function of their volume concentration in the gas sampled, and of the flow rate of that gas through the pump 60, the beat frequency detected by the counter 67 will vary linearly with time. To simplify further computational procedures, the output of the counter is converted to an analog voltage in a digital-to-analog converter 68 and recorded, as a function of time, by a recorder 65, suitably of the strip chart type. The signal, either in the digital form, or as an analog voltage, may also be passed to a computer for further processing.

The total particulate mass of the air sample may be determined by diverting a portion of the air in line *62a* through the channel *62d* to a beta gauge 70, as described above in connection with FIG. 2. Alternatively, separate air samples may be taken for the total mass determination.

Where the mass fraction of the total aerosol content of the gaseous medium is not known from independent measurements, the filter 63 is removed at the end of the measurement period and the accretion of particulate determined by weighing. The calculation of the water content is a straightforward procedure, once the frequency shift corresponding to a given total aerosol content is known. Instruments constructed according to the teachings of this disclosure have been built and operated according to the method set forth herein; reasonable and useful results were obtained in a variety of environmental conditions with sampling flow rates of the order of one cubic meter per hour and total sampling periods of the order of 20 minutes. The determination of the total particulate content of the sampled gas and of the dielectric constant of the solid constituents therein have been made using methods known in the art and form no part of the invention.

The instrument of the invention has been disclosed herein with reference to alternate embodiments; other changes in the physical and/or the electronic arrangements associated therewith are possible and may suggest themselves to one skilled in the art upon exposure to the teachings herein. Such changes are deemed to be encompassed by the invention which is limited only by the appended claims.

I claim:

1. A method for determining the mass concentration of water in the liquid phase entrained as an aerosol in a gaseous medium, utilizing a cavity with a known resonant frequency when irradiated with microwave energy, means for generating a microwave signal adapted to irradiate said cavity, and means for determining the instantaneous resonant frequency of said cavity, comprising the steps of:

drawing said gaseous medium through said cavity at a predetermined volumetric rate;

entrapping the particulate content in said gaseous medium centrally in said cavity;

irradiating said cavity with a signal produced in said means for generating a microwave signal;

monitoring the variation with time of the instantaneous resonant frequency of the cavity, as excited by said irradiating signal and modified by the presence of said particulate;

determining the mass of said particulate fraction in a given volume of said gaseous medium;

determining the dielectric constant of the solid constituents of said particulate fraction; and computing the mass rate of accretion of liquid water in said cavity from the monitored variation of its resonant frequency with time and the accretion rate of total particulate content within said cavity.

2. The method of claim 1, wherein said gaseous medium is atmospheric air.

3. The method of claim 1, further comprising the steps of:

drawing said gaseous medium through a second cavity, identical in shape, size and resonant qualities to said cavity with a known resonant frequency, after the entrapment of said particulate fraction;

irradiating said second cavity with a microwave signal;

monitoring the time rate of change of the resonant frequency of said second cavity; and comparing the variation with time of the resonant frequencies of both cavities, prior to said step of computing the mass rate of accretion of liquid water, to remove from the aforementioned measurement second order changes attendant upon environmental changes influencing both of said cavities.

4. Apparatus for the measurement of the mass concentration of water in the liquid phase entrained in a gaseous medium as an aerosol, comprising:

an enclosure defining a resonant cavity for microwave radiation;

a vacuum pump, adapted to ingesting said gaseous medium;

channel means interconnecting the intake of said pump with a volume containing said gaseous medium, constructed from a material substantially transparent to said microwave radiation, said channel passing through the geometric center of said cavity;

filter means in said channel means, at the geometric center of said cavity, adapted to entrapping aerosol particles entrained in said gaseous medium;

mass determinator means for measuring the mass of the aerosol particles trapped on said filter means;

generator means, for microwave signals in the frequency range encompassing the resonance of said cavity;

detector means for resonant mode of microwave radiation within said cavity; and means for injecting signals generated by said generator means into said cavity.

5. Apparatus according to claim 4, wherein said enclosure defines a cavity in the form of a right circular cylinder.

6. Apparatus according to claim 4, additionally comprising tuning means for altering resonant frequency of said cavity.

7. Apparatus according to claim 4, further comprising means for controlling the temperature of said enclosure.

8. Apparatus according to claim 4, wherein said detector means comprise means for measuring the instantaneous resonant frequency of said cavity, and means for producing a signal proportional in magnitude to said frequency.

9. Apparatus for the measurement of the mass concentration of water in the liquid phase, entrained in a gaseous medium as an aerosol, comprising:

a pump, adapted to ingesting said gaseous medium;

a first enclosure, defining a first cavity resonant to microwave radiation;

a second enclosure, identical in shape, size and material to said first enclosure, defining a second cavity;

channel means interconnecting the intake of said pump with a volume containing said gaseous medium, constructed from a material substantially transparent to said microwave radiation, said channel passing through the geometric centers of said first and said second enclosures, in succession;

filter means in said channel means, at the geometric center of said first enclosure, adapted to entrapping aerosol particles entrained in said gaseous medium;

first generator means, for microwave signals in the frequency range encompassing the resonance of said first cavity, conductively interconnected therewith;

second generator means, for microwave signals in the frequency range encompassing the resonance of said second cavity, conductively interconnected therewith;

comparator means, for comparing resonant frequencies of said first and second cavities, excited by signals generated by said first and second generator means, respectively;

mass determinator means for measuring the mass of entrapped aerosol particles on said filter means; and monitoring means for the output signal of said comparator means, for monitoring instantaneous frequency differential between said first and second cavities as particulate entrapped by said filter means collects in said first cavity.

10. The apparatus of claim 9, wherein said first enclosure defines a cavity in the shape of a right circular cylinder.

11. The apparatus of claim 9, wherein said gaseous medium is atmospheric air.

* * * * *